US006225118B1

(12) United States Patent
Grant et al.

(10) Patent No.: US 6,225,118 B1
(45) Date of Patent: May 1, 2001

(54) MULTICELLULAR IN VITRO ASSAY OF ANGIOGENESIS

(75) Inventors: Eileen T. Grant, Aberdeen; Graham T. Bell, Inveruri; Stephen Bloor, Chorley, all of (GB)

(73) Assignee: Biocure Limited (GB)

( * ) Notice: Subject to any disclaimer, the term of this patent is extended or adjusted under 35 U.S.C. 154(b) by 0 days.

(21) Appl. No.: 09/164,659

(22) Filed: Oct. 1, 1998

Related U.S. Application Data
(60) Provisional application No. 60/067,518, filed on Dec. 4, 1997.

(30) Foreign Application Priority Data
Oct. 1, 1997 (GB) ................................................. 9720987

(51) Int. Cl.$^7$ .............................. C12N 5/06; C12N 5/00; C12N 5/02; C12Q 1/00; G01N 33/53
(52) U.S. Cl. .............................. 435/347; 435/4; 435/373; 435/377; 435/383; 435/975
(58) Field of Search ........................... 435/7.1–7.2, 7.23, 435/347, 373, 4, 377, 383, 975; 436/64; 530/387.7, 387.9, 388.8

(56) References Cited

U.S. PATENT DOCUMENTS

| 4,539,716 | 9/1985 | Bell | 623/1 |
|---|---|---|---|
| 4,546,500 | 10/1985 | Bell | 623/1 |
| 5,160,490 | 11/1992 | Naughton et al. | 435/284 |
| 5,804,178 | 9/1998 | Vacanti | 424/93.7 |
| 5,830,708 | 11/1998 | Naughton | 435/70.1 |

FOREIGN PATENT DOCUMENTS

| 0358506 | 3/1990 | (EP) . |
|---|---|---|
| WO95/23968 | 9/1995 | (WO) . |
| WO96/40175 | 12/1996 | (WO) . |

OTHER PUBLICATIONS

Yamashita et al, Comp.Biochem.Physiol.; 1994 vol. 109A (1) pp. 101–110.*

Zhang et al, Proc Annu Mett Am Assoc Cancer Res; 35:A1105, 1994.*

DeLisser et al, Amer. Jnl. Path, Sep. 1997, vol. 151 (3) pp. 671–677.*

Villaschi et al. "Paracrine Interactions Between Fibroblasts and Endothelial Cells in a Serum–Free Coculture Model" *Lab. Invest.* 71, 291–299 (1994).

Montesano et al. "Paracrine induction of angiogenesis in vitro by Swiss 3T3 fibroblasts" *J. Cell Sc.* 105, 1013–1024.

Kuzuya et al. "Induction of Endothelial Cell Differentiation in Vitro by Fibroblast–Derived Differentiation . . . " *Exp. Cell Res.* 215, 310–318 (1994).

Nehls et a. "A microcarrier–based cocultivation system for the investigation of factors and cells . . . " *Histochem Cell Biol.* 104, 459–466 (1995).

Bussolino et al. "Molecular mechanisms of blood vessel formation" *Trends in Biochem. Sci.* 22, 251–256 (1997).

* cited by examiner

*Primary Examiner*—Susan Ungar
*Assistant Examiner*—Gary B. Nickol
(74) *Attorney, Agent, or Firm*—Heslin & Rothenberg, P.C.

(57) ABSTRACT

A multicellular in vitro assay for modeling the combined stages of angiogenesis namely the proliferation, migration and differentiation stages of cell development, wherein the assay comprises providing a dual culture of endothelial cells together with another cell-type exhibiting interaction therewith to display the combined stages of angiogenesis in vitro.

9 Claims, 3 Drawing Sheets

ANGIOGENESIS ASSAY

ANGIOGENESIS ASSAY

(ORIGINAL MAGNIFICATION) x 7500

MULTICELLULAR IN VITRO ASSAY OF ANGIOGENESIS

CROSS REFERENCE TO RELATED APPLICATIONS

This application claims the priority of U.S. provisional application No. 60/067,518, filed Dec. 4, 1997, now abandoned, and United Kingdom application 9720987.8, filed Oct. 1, 1997, the complete disclosures of which are incorporated herein by reference.

FIELD OF THE INVENTION

This invention relates to an in vitro assay of angiogenesis and in particular a multicellular in vitro assay of angiogenesis.

BACKGROUND OF THE INVENTION

Most populations of differentiated cells in vertebrates are subject to turnover through cell death and renewal. Some fully differentiated cells such as hepatocytes in the liver and endothelial cells lining the blood vessels simply divide to produce daughter cells of the same differentiated type. The proliferation rate of such cells is controlled to maintain the total number of cells. Thus if a large part of the liver is destroyed then the remaining hepatocytes increase their division rate in order to restore the loss.

Endothelial cells form a single cell layer that lines all blood vessels and regulates exchanges between the blood stream and the surrounding tissues. New blood vessels develop from the walls of existing small vessels by the outgrowth of these endothelial cells which have the capacity to form hollow capillary tubes even when isolated in culture. In vivo, damaged tissues and some tumors attract a blood supply by secreting factors that stimulate nearby endothelial cells to construct new capillary sprouts. Tumors that fail to attract a blood supply are severely limited in their growth.

The process whereby new vessels originate as capillaries, which sprout from existing small vessels, is called angiogenesis. It can therefore be seen that angiogenesis plays a major role in normal tissue development and repair and in the progression of some pathological conditions.

Once the vascular system is fully developed, endothelial cells of blood vessels normally remain quiescent with no new vessel formation. If disease or injury occurs, the formation of new blood vessels can proceed normally, as in natural wound healing, or be insufficient, as in chronic dermal ulcers, or there is deregulation of growth and an abnormal increase in vessel density ensues as in tumorogenesis, diabetic retinopathy, psoriasis and inflammation. Inhibition of inappropriate angiogenesis or enhancement of angiogenesis in non-healing wounds is therefore an extremely important target for drug discovery programs. However, research in this area leading to new drug development has been hindered by the lack of in vitro models of angiogenesis.

Angiogenesis is an extremely complex process involving a wide range of growth factors, extracellular matrix molecules, enzymes and various cell types. Such a complexity of relationships has resulted in major difficulties in developing an in vitro assay which models the entire in vivo process. Angiogenesis can be subdivided into three phases: proliferation, migration and differentiation. Assays exist which model each of these phases separately. Simple in vitro tests measure changes in proliferation of a range of cell types and assess migration over basement membrane proteins. Current in vitro assay systems, which depend on provision of a protein matrix, effectively measure the ability of endothelial cells to differentiate. Assay systems measuring differentiation involve the formation of cord-like structures by endothelial cells. All such systems depend on supplying the cells with exogenous basement membrane proteins on which the cells migrate to form tubules. Cell migration occurs over relatively short time periods of 2–16 hours to give a three dimensional structure. In addition to the basement membrane proteins, many of the systems require the provision of growth factors to produce acceptable tubule formation. The time scale over which tubules are formed provides an excellent test for inhibition of differentiation but is not so useful when testing for enhancement.

The assay systems described above come closest to modeling angiogenesis but none of them combine all three of the stages required for angiogenesis.

SUMMARY OF THE INVENTION

The object of the present invention is to obviate or mitigate the aforesaid disadvantages of current methodologies by providing an in vitro assay of angiogenesis which encompasses the three stages of angiogenesis and which can be used to examine both stimulation and inhibition of angiogenesis.

One aspect of the present invention relates to a multicellular in vitro assay for modeling the combined stages of angiogenesis, namely, the proliferation, migration and differentiation stages of cell development. The assay provides for a dual culture comprising endothelial cells together with another cell-type which will interact with the endothelial cells to display the combined stages of angiogenesis in vitro. The multicellular in vitro assay for modeling the combined stages of angiogenesis comprises:

(i) providing a culture of endothelial cells;
(ii) adding to the culture of endothelial cells another cell-type exhibiting interaction therewith; and
(iii) growing a dual culture of endothelial cells and another cell-type to display the combined stages of angiogenesis in vitro.

When the other cell type exhibiting interaction with endothelial cells is a fibroblast, the resulting dual culture of fibroblasts and endothelial cells requires no additional growth factors other than those present in standard culture medium. It is postulated that the interaction of these cell types is dependent on cell signaling mechanisms therebetween. The non-reliance on additional growth factors is remarkable and unanticipated considering past research on the subject. In this aspect the invention can be characterized as a multicellular in vitro assay for modeling the combined stages of angiogenesis comprising the steps of (a) setting up growth containers suitable for sustaining dual cell cultures and having a suitable culture medium for sustaining at least growth of endothelial cells therein; (b) seeding a dual culture of human fibroblasts and human endothelial cells into the growth containers; (c) incubating the dual culture, without the provision of any exogenous growth factors, from an initial proliferation phase until a confluent monolayer is produced. The growth medium is replaced at regular intervals, such as every 48 hours, to achieve optimal development.

In a related aspect, the present invention relates to a method of screening agents for their ability to promote or inhibit angiogenesis. The method comprises co-culturing endothelial cells with another cell-type, for example, interstitial cells such as fibroblasts, which will interact to display the combined stages of angiogenesis, and introducing the agent to be screened in controlled amounts to the cultures and monitoring angiogenesis in the cultures. The screening method may be readily automated and angiogenesis may be monitored by known automated counting techniques, image analysis or by spectrographic methods. The multicellular in vitro assay for screening agents that alter angiogenesis comprises: (a) cultivating in a plurality of test containers a plurality of co-cultures of endothelial cells together with another cell-type exhibiting interaction therewith to display the combined stages of angiogenesis; (b) adding an agent to at least one of the cultures; (c) allowing the plurality of cultures to grow; and (d) comparing the culture containing the agent to another of the plurality of cultures not containing the agent.

In yet another aspect, the invention relates to an assay kit including a vessel provided with culture medium appropriate for sustaining fibroblasts and endothelial cells, and seeded with said cells as a dual culture, wherein the cells are preferably Human Adult Dermal Fibroblasts and Human Umbilical Vein Endothelial Cells (HUVEC) respectively. The kit is useful in a multicellular in vitro assay for modeling the combined stages of angiogenesis. It comprises: (a) a vessel; (b) a culture medium appropriate for sustaining fibroblasts and endothelial cells within the vessel; and (c) a dual culture of fibroblasts and endothelial cells In one embodiment the essay comprises the steps of (a) setting up growth containers suitable for sustaining dual cell cultures and having a suitable culture medium for sustaining at least growth of endothelial cells therein; (b) seeding a dual culture of interstitial cells, such as human fibroblasts, and human endothelial cells to obtain an interstitial cell:endothelial cell ratio in the range of 2:1 to 8:1; (c) incubating same without the provision of any exogenous growth factors; (d) monitoring the progress of the cells from an initial proliferation phase until a confluent monolayer is produced; and (e) changing the culture medium at regular intervals throughout the proliferation, migration and differentiation stages of the cell development. Preferably the fibroblasts are Human Adult Dermal Fibroblasts and the endothelial cells are Human Umbilical Vein Endothelial Cells (HUVEC), and the cell ratio in the dual culture of Human Adult Dermal Fibroblasts to Human Umbilical Vein Endothelial Cells (HUVEC) is from about 2:1 to 8:1. Advantageously the culture medium of the dual culture is changed every 48 hours. Preferably the vessel contains a cell ratio of Human Adult Dermal Fibroblasts to Human Umbilical Vein Endothelial Cells (HUVEC) of about 2:1 to 8:1.

A preferred test kit for use in a multicellular in vitro assay comprises a culture vessel seeded with a dual culture of Human Adult Dermal Fibroblasts and Human Umbilical Vein Endothelial Cells (HUVEC) having a cell ratio of about 2:1 to 8:1, the kit further comprises at least one of, and preferably all of: a growth medium capable of sustaining endothelial cell growth, a fixative, a blocking buffer, a washing buffer, and reagents and antibodies for suitable visualization. Reagents for visualization may include those used in von Willebrand Immunoassay or PECAM-1 Immunoassay.

According to a further aspect of the present invention there is provided a multicellular in vitro assay comprising a dual culture of endothelial cells and fibroblasts, preferably Human Adult Dermal Fibroblasts and Human Umbilical Vein Endothelial Cells (HUVEC) and being sustainable in a culture medium, said culture medium capable of sustaining at least endothelial cell growth, the dual culture having been seeded with a cell ratio of about 2:1 to 8:1 of Human Adult Dermal Fibroblasts to Human Umbilical Vein Endothelial Cells (HUVEC) wherein the assay is used to model in vivo angiogenesis for use particularly in the likes of drug research or tumor therapy whereby an inhibition of the angiogenesis model by a test drug would indicate its suitability for use in tumor therapy. An enhancement of the angiogenesis model by a test drug would indicate its suitability for use as a wound healing agent.

By virtue of this invention there is provided a multicellular in vitro assay which enables examination and modeling for each stage of angiogenesis namely each of the proliferation, migration and differentiation stages of cell development.

BRIEF DESCRIPTION OF THE DRAWINGS

FIGS. 1a, 1b and 1c show the development of the tubules over a period of 1, 7 and 14 days FIG. 1a: Day 1. The darkly stained HUVEC are clearly visible, positioned on the surface of the fibroblast monolayer. (×85).

The cultures of FIGS. 2a and 2b were incubated for 14 days and are therefore directly comparable to FIG. 1c.

Visualization in FIGS. 1–3 are by von Willebrand factor immunoassay, using DAB substrate, and hematoxylin counterstain.

DETAILED DESCRIPTION OF THE INVENTION

In accordance with the present invention there is provided an in vitro assay for angiogenesis dependent on appropriate cell signaling mechanisms using a dual culture and requiring no additional growth factors. Both stimulation and inhibition of angiogenesis can be demonstrated using this technique.

Furthermore the assay system of the present invention combines all three stages of angiogenesis namely proliferation, migration and differentiation.

The assay system involves co-culture of Human Umbilical Vein Endothelial Cells (HUVEC) with Human Adult Dermal Fibroblasts. Under the conditions provided the cells form a series of anastomosed tubules.

The Human Umbilical Vein Endothelial Cells (HUVEC) are commercially available from suitable outlets and in this case are bought in cryopreserved form. Prior to employment in the tubule assay, the cells are routinely passed and cultured in any suitable commercially available Endothelial Growth Medium, EGM, containing 2% foetal calf serum. The HUVEC are used at passes 2 to 6 in the assay.

The Human Adult Dermal Fibroblasts are cultured from skin samples which may be obtained from local hospitals. Prior to employment in the tubule assay, the cells are routinely passed and cultured in Dulbecco's Modified Eagle's Medium, DMEM, plus 10% foetal calf serum. The fibroblasts are used at passes 6 to 10 in the assay.

The tissue culture treated vessels to be used in the assay are equilibrated by pre-incubation with EGM, plus and minus treatments, for a period of 30 minutes at 37° C., 5% $CO_2$ humidified atmosphere. Although 12-well and 24-well tissue culture treated plates are normally used, others may equally well be employed and the volumes added are 1 ml per well for 12 well plates and 0.5 ml per well for 24-well plates. The cells are harvested using any suitable commercially available Trypsin solution for fibroblasts and any suitable commercially available Trypsin-EDTA solution for HUVEC. The cells are resuspended in EGM and counted. Immediately before use, the cells are expressed through a syringe and needle (23G×1¼) to ensure good dispersal. The techniques and materials involved in culturing endothelial cells are well known to persons of skill in the art, and are readily available from standard texts.

The two types of cell are thoroughly mixed at the required densities and seeding ratio (which can be between 2:1 and 8:1, fibroblasts to HUVEC) and added to the plates. In order to ensure an even distribution over the growth surface, the plates are gently agitated in a random fashion. This prevents a pooling of cells in the center of the wells.

Cell ratios of fibroblasts to endothelial cells in the 2:1 to 8:1 range are optimal. Seeding density determines the number of days of growth available before reaching a cell density at which inhibition of growth sets in. The optimum initial density is one which is low enough to allow for 14 days of growth without evidence of inhibition. The optimal cell ratio and seeding density can vary somewhat with the HUVEC line employed, but the person of skill can readily determine the optimal values for tubule formation by routine experimentation.

The co-cultures are normally incubated over a period of 14 days with complete medium changes approximately every two days. Rudimentary tubule development is evident from around day 4, but, as with all cell types, variations can occur and tubules may form earlier. The whole process can be accelerated to a seven day period or less by increasing the seeding densities whilst maintaining the established ratio. This, however, is not always desirable as the effects of any treatments may be better seen over the long term rather than the short term.

To monitor the progress of the assay, four time points are normally used over a 14 day growth period. This may be altered to suit requirements. At each time point the medium is discarded from the growth vessel and the cells fixed in cold (−20° C.) 70 ethanol for 30 minutes at room temperature. At this point the plate may be washed and stored in phosphate buffered saline at 4° C. until completion of the experiment when all the cultures are developed the same time, or each time point may be processed separately.

Visualization of the tubules is accomplished most readily by an immunoassay that targets a cell marker on one or both of the cells being cultured. In the case of the HUVEC line, two cell markers that may be employed are the glycoprotein von Willebrand factor and the cell adhesion molecule PECAM-1. Human von Willebrand factor (factor VIII R:Ag) is a multimeric plasma glycoprotein. It mediates platelet adhesion to vessel walls and serves as a carrier and stabiliser for coagulation factor VIII. The factor is synthesized constitutively by endothelial cells. Platelet Endothelial Cellular Adhesion Molecule or PECAM-1 is a 130-KD integral membrane glycoprotein that is the member of the Ig super family and is found constitutively on the surface of endothelial cells, particularly at intercellular junctions. It is also expressed on the surface of platelets and leukocytes.

The immunoassay process involves a two step, indirect method in which an enzyme-conjugated secondary antibody reacts with an unlabelled primary antibody bound to the cell marker. A substrate solution is added, which reacts with the enzyme complex to produce an insoluble, coloured end product. In this way the endothelial tubules are visualised. The co-cultures may be counterstained with hematoxylin nuclear stain. This aids visualization of the fibroblast monolayer.

Quantitative assessment of the tubules may be achieved by a variety of methods, ranging from manual counting to video imaging and computerised image analysis.

Figure 1A:
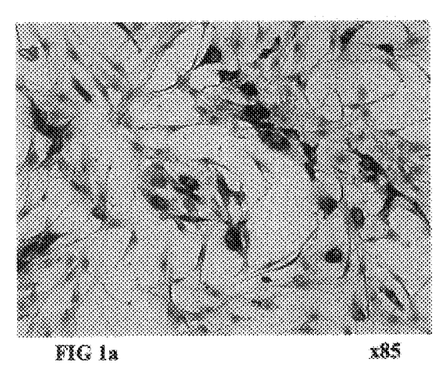
Figure 1B:
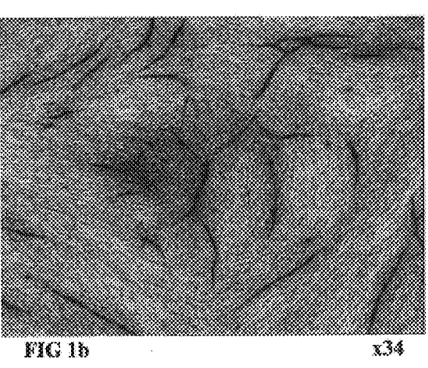
FIG. 1b: Day 7. Thread-like tubules are forming in the confluent fibroblast monolayer. (×34).
Figure 1C:
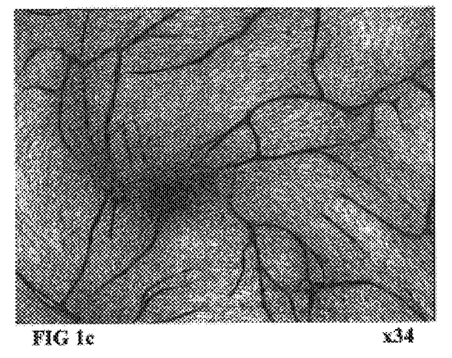
FIG. 1c: Day 14. An intricate network of thickened, anatomizing vessels has formed, many originating from areas with high fibroblast concentration. (×34)

When the HUVEC cells and fibroblasts are incubated together in co-culture without the addition of any exogenous growth factors, but with the complete replacement of the culture medium every two days, the cells initially pass through a proliferative stage which continues until a confluent monolayer is produced. At day 1 the culture consists of a background of fibroblasts with small islands of endothelial cells (FIG. 1a). The endothelial cells, continuing to proliferate, enter a migratory phase where they can be seen to move within the fibroblast layer to form thread-like tubular structures at approximately day 7 (FIG. 1b). These structures eventually extend and join up to form an intricate network resembling the capillary bed of the chick chorioallantoic membrane at about day 14 (FIG. 1c). The "vessels" formed by this process can often be seen to originate from the islands of HUVEC formed during the proliferative phase. High concentrations of fibroblasts are nearly always visible in the area from which the HUVEC have migrated. By day 14 the tubules are wider and thicker with patent lumina which can be visualised with phase-contrast microscopy.

Both the seeding density of the two cell types and the ratio of HUVEC to fibroblasts influence the progression of tubule development, as does the rate at which the HUVEC divide. By using HUVEC which have widely differing doubling times it can be seen that when the doubling time is short, and therefore the HUVEC are growing very quickly, the outcome tends to be large islands of undifferentiated HUVEC. This suggests that there is a certain point during the process at which intercellular signals between fibroblast and HUVEC initiate differentiation.

Experiments were also carried out to illustrate the use of the assay to show the inhibition or stimulation of angiogenesis by a sample under test, for example for testing the effects of new drugs.

Figure 2A:
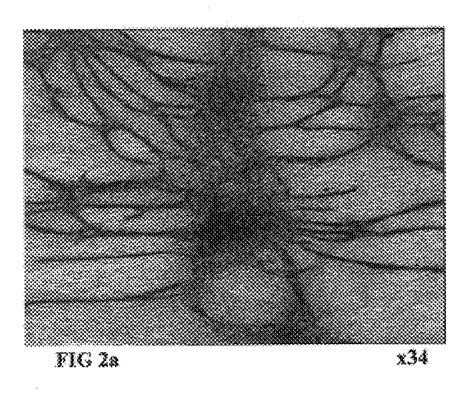
FIG. 2a demonstrates a marked increase in tubule formation on addition of human recombinant vascular endothelial growth factor (VEGF), 10 ngml$^{-1}$. (×34).

Vascular endothelial growth factor (VEGF) is a recognized mitogen of endothelial cells that stimulates angiogenesis. Manipulation of the in vitro system was confirmed by adding human recombinant VEGF at the start of the experiment and at each medium change. As a result, tubule formation was much enhanced with networks of numerous arcades (FIG. 2a).

Figure 2B:
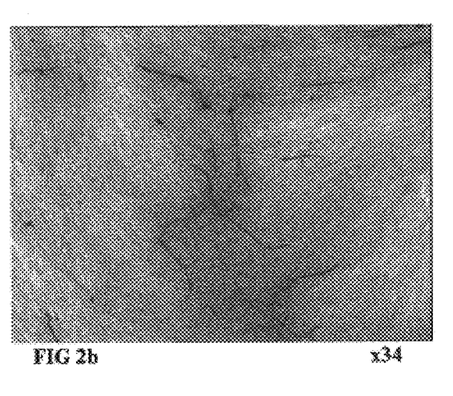
FIG. 2b demonstrates a marked decrease in tubule formation on addition of anti-human recombinant VEGF neutralizing antibody, 10 ngml$^{-1}$ in combination with human recombinant VEGF 10 ngml$^{-1}$ (×34).
Figure 3A:
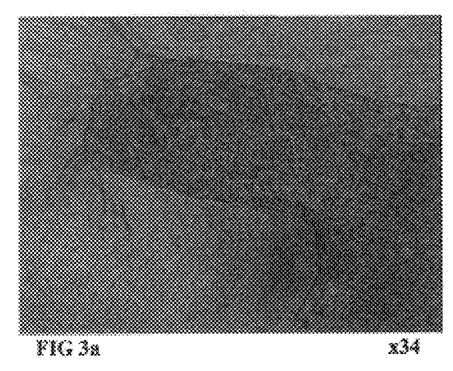
FIG. 3a: Incubation with U-87-MG conditioned medium leads not only to the inhibition of tubule formation but also to a massive increase in the number of HUVEC. Note some tubules form at the edges of the large HUVEC "islands". (×34).
Figure 3B:
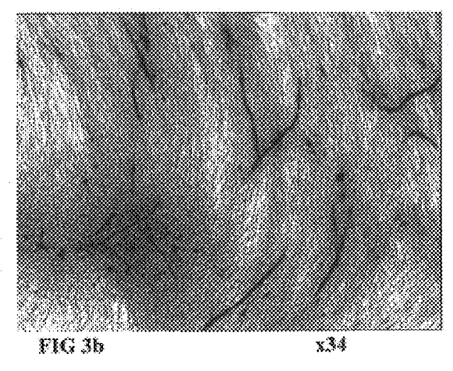
FIG. 3b: Incubation with GO-G-CCM conditioned medium effects a marked reduction in HUVEC proliferation. Those cells present, however, have formed small lengths of tubules. (×34)
Figure 4:
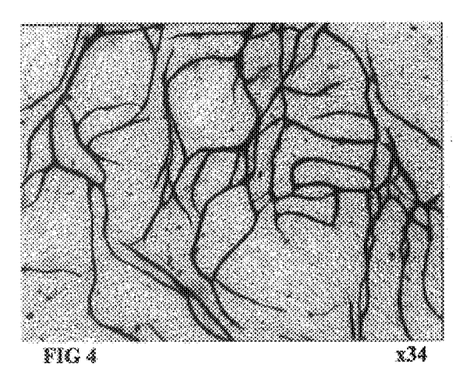
FIG. 4 shows an image of tubule formation at day 14, developed by the PECAM-1 immunoassay using BCIP/NBT substrate (alkaline phosphatase compatible). (×34)

Conversely, when anti-human recombinant VEGF neutralising antibody was added with VEGF, tubule formation was markedly reduced (FIG. 2b). The system was also tested using conditioned medium (serum free) from various tumor cell lines including that from U-87-MG (human glioblastoma cell line) which was available from the local hospital and GO-G-CCM (human brain astrocytoma) available from the European Collection Of Animal Cell Cultures (ECACC), for it has been hypothesized that tumor cells can control angiogenesis and in turn favor growth. U-87-MG caused a massive proliferation of HUVEC with very little tubule formation (FIG. 3a) whereas GO-G-CCM much reduced HUVEC proliferation and tubule formation (FIG. 3b). These results demonstrate the flexibility of the assay and the response to materials which have different modes of action. In this way the assay can be used to screen for inhibitors and enhancers of angiogenesis.

Figure 5:
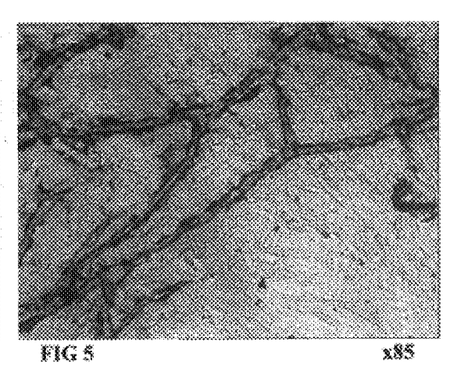
FIG. 5 shows an image of Collagen IV expression in the tubules at day 14. (×85)

In FIG. 5 there is shown an image of Collagen IV expression in the tubules at day 14. In vivo, extra cellular matrix proteins are laid down by the developing capillaries of neovasculature, and this in vitro image shows that Collagen IV is selectively expressed by the endothelial cells. This is further evidence that the assay is indeed mimicking the in vivo development of vessels.

Figure 6:
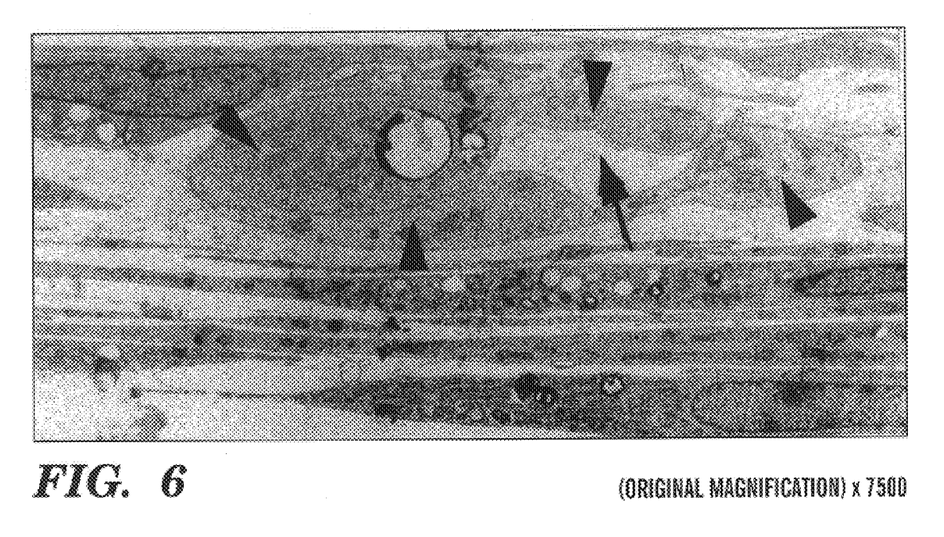
FIG. 6 is a photographic image of a vertical cross section of the cell layer in the tubuleassay at day 14 as seen through the electron microscope (original magnification ×7,500).

FIG. 6 shows a photographic image of a vertical cross section of the cell layer in the tubule assay (day 14) as seen through an electron microscope (original magnification×7,500). This quite clearly shows a tubule composed of several endothelial cells (shown by arrowheads) encompassing a central lumen (shown by arrow). This presents further proof that the assay is in fact producing tubules with a central "cavity" or lumen.

A control study was also set up to show that not all cells would function if substituted for those currently used in the assay of the present invention. The control study showed HUVEC co-cultured with human umbilical artery smooth muscle cells (HUASMC), cells which form a close association with the endothelial cells in vivo. No tubules formed.

It is envisaged that the above invention will give a more accurate study of in vivo angiogenesis by using the in vitro model for experiments to see the effect of various external factors on same. For example, studying the effect of particular drugs (particularly in the field of tumor therapy) will be greatly assisted by this invention. The assay can be used to determine whether the particular drug under test would inhibit angiogenesis, thereby inhibiting tumor growth, or whether it would enhance angiogenesis, thereby having applications in wound healing therapy. In vivo, damaged tissues and some tumors attract a blood supply by secreting factors that stimulate nearby endothelial cells to construct new capillary sprouts. It can therefore be shown by using this assay whether a particular test drug can prevent the stimulation of the endothelial cells, thereby preventing the tumors from attracting a blood supply. Tumors that fail to attract a blood supply are severely limited in their growth. The present invention is also extremely valuable in the study of angiogenesis per se.

It is also envisaged that culture vessels will be seeded with viable co-cultures which will be grown up at the preferable cell ratio of between about 2:1 and 8:1, fibroblasts to HUVEC. After approximately 24 hours of co culture the vials would then be suitably packaged in the form of a kit. The kit will also contain the necessary ingredients required to keep the co-culture viable, such as a standard ECM, and also for visualization of results by means of von Willebrand Immunoassay or PECAM-1 Immunoassay).

The preferred test kit for use in the multicellular in vitro assay has a culture vessel seeded with a dual culture of Human Adult Dermal Fibroblasts and Human Umbilical Vein Endothelial Cells (HUVEC) having a cell ratio of about 2:1 to 8:1, a quantity of growth medium capable of sustaining endothelial cell growth, fixative, blocking buffer, washing buffer and the reagents and antibodies for suitable visualization by von Willebrand Immunoassay or PECAM-1 Immunoassay Therefore the kit will also contain the following components for use in a von Willebrand Immunoassay:

(i) a primary antibody—rabbit anti-human von Willebrand Factor;
(ii) a secondary antibody—goat anti-rabbit IgG (whole molecule) Horse radish Peroxidase conjugate; and
(iii) a substrate—Horse radish Peroxidase substrate with insoluble end product; and the following components for use in a PECAM-1 Immunoassay:
(i) a primary antibody—mouse anti-human PECAM-1;
(ii) a secondary antibody—goat anti-rabbit IgG (whole molecule) Alkaline Phosphatase conjugate; and
(iii) a substrate—Alkaline Phosphatase substrate with insoluble end product.

What is claimed is:

1. A multicellular in vitro assay method for modeling angiogenesis comprising:
   (a) mixing a suspension of human fibroblasts with a suspension of human umbilical vein endothelial cells in a ratio of from about 2:1 to 8:1 to provide a mixture of cells, both of said endothelial cells and said fibroblasts being suspended in endothelial growth medium:
   (b) culturing said mixture of cells, whereby the fibroblasts form a monolayer in which the endothelial cells display proliferation, migration and differentiation into networks of tubules.

2. A method according to claim 1 wherein the endothelial growth medium is changed about every 48 hours.

3. A method according to claim 1 wherein the proliferation, migration and differentiation are monitored by image analysis.

4. An assay kit comprising:
   (a) a growth container;
   (b) endothelial growth medium;
   (c) a suspension of human umbilical vein endothelial cells (HUVEC); and
   (d) a suspension of fibroblasts in a ratio of about 2:1 to 8:1 with respect to said human umbilical vein endothelial cells (HUVEC).

5. An assay kit comprising:
   (a) a growth container; said container containing
   (b) a living culture of human fibroblasts and human umbilical vein endothelial cells (HUVEC) in endothelial growth medium; said living culture arising from the culture of an initial mixture of human fibroblasts and human umbilical vein endothelial cells (HUVEC) in a ratio of about 2:1 to 8:1 grown for a period of about 24 hours from initial mixing of said fibroblasts and endothelial cells and then suitably packaged.

6. A kit according to claim 5 additionally comprising one or a plurality of containers containing an additional quantity of said endothelial growth medium.

7. A kit according to any of claims 4 to 6 additionally comprising fixative for assisting in subsequent visualization, blocking buffer, washing buffer, reagents and antibodies for visualization.

8. A kit according to claim 7 wherein the reagents for visualization are those for use in a von Willebrand Immunoassay.

9. A kit according to claim 7 wherein the reagents for visualization are those for use in a Platelet Endothelial Cellular Adhesion Molecule (PECAM-1) Immunoassay.

* * * * *

UNITED STATES PATENT AND TRADEMARK OFFICE
CERTIFICATE OF CORRECTION

PATENT NO. : 6,225,118 B1
DATED : May 1, 2001
INVENTOR(S) : Grant et al.

It is certified that error appears in the above-identified patent and that said Letters Patent is hereby corrected as shown below:

Column 4,
Line 29, delete "10 ngml$^{31\ 1}$" and replace with -- 10ngml$^{-1}$ --.
Line 32, delete "10 ngml$^{31\ 1}$" and replace with -- 10ngml$^{-1}$ --.

Column 8,
Line 28, delete "anti-rabbit" and replace with -- anti-mouse --.

Signed and Sealed this

Eighth Day of January, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO. : 6,225,118 B1  Page 1 of 1
DATED : May 1, 2001
INVENTOR(S) : Grant et al.

It is certified that error appears in the above-identified patent and that said Letters Patent is hereby corrected as shown below:

Title page,
Item [75], Inventorship Address,
Line 2, "Inveruri" and insert -- Inverurie --.

Column 5,
Line 65, after 70, insert -- % --.

Signed and Sealed this

Fifth Day of February, 2002

Attest:

JAMES E. ROGAN
*Attesting Officer*   *Director of the United States Patent and Trademark Office*